United States Patent
Kim et al.

(10) Patent No.: US 11,510,868 B2
(45) Date of Patent: Nov. 29, 2022

(54) SMART CONTACT LENS FOR NON-INVASIVE DRUG DELIVERY

(71) Applicant: KOREA INSTITUTE OF SCIENCE AND TECHNOLOGY, Seoul (KR)

(72) Inventors: Jinseok Kim, Seoul (KR); Yong-Won Song, Seoul (KR); Hyungdal Park, Seoul (KR); Ockchul Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 246 days.

(21) Appl. No.: 16/672,518

(22) Filed: Nov. 4, 2019

(65) Prior Publication Data
US 2020/0138702 A1    May 7, 2020

(30) Foreign Application Priority Data
Nov. 6, 2018 (KR) .......................... 10-2018-0134848

(51) Int. Cl.
  *A61F 9/00*   (2006.01)
  *A61K 9/00*   (2006.01)
  *A61N 1/04*   (2006.01)
  *A61N 1/32*   (2006.01)
  *G02C 7/04*   (2006.01)

(52) U.S. Cl.
CPC .......... *A61K 9/0051* (2013.01); *A61F 9/0017* (2013.01); *A61K 9/0009* (2013.01); *A61N 1/0448* (2013.01); *A61N 1/325* (2013.01); *G02C 7/04* (2013.01)

(58) Field of Classification Search
CPC ... A61F 9/0017; A61K 9/0009; A61K 9/0048; A61K 9/0051; A61N 1/303; A61N 1/325; G02C 7/04
See application file for complete search history.

(56) References Cited

U.S. PATENT DOCUMENTS

| | | | |
|---|---|---|---|
| 8,273,366 B2 | 9/2012 | Chauhan et al. | |
| 8,755,880 B2* | 6/2014 | Higuchi | A61N 1/044 |
| | | | 604/20 |
| 10,302,964 B2 | 5/2019 | Kim et al. | |
| 10,980,830 B2* | 4/2021 | Kuefner | A61L 15/58 |
| 2007/0106278 A1 | 5/2007 | Higuchi et al. | |

(Continued)

FOREIGN PATENT DOCUMENTS

| JP | 2008529606 A | 8/2008 |
|---|---|---|
| JP | 2018502639 A | 2/2018 |

(Continued)

OTHER PUBLICATIONS

Joseph B. Ciolino et al., "Contact Lenses for Drug Delivery," Seminars in Ophthalmology, 2009, pp. 156-160, vol. 24, Informa Healthcare USA, Inc.

*Primary Examiner* — Deanna K Hall
(74) *Attorney, Agent, or Firm* — Cantor Colburn LLP

(57) ABSTRACT

Provided is a smart contact lens for non-invasive drug delivery including a platform configured to be worn on an eye, a reservoir installed within the platform, and having a receiving part in which a drug is received, to provide the eye with the drug, an electrode for iontophoresis installed in the reservoir to make iontophoresis work, to provide the eye with the drug from the reservoir, and an activation chip electrically connected to the electrode for iontophoresis to activate iontophoresis.

4 Claims, 5 Drawing Sheets

(56) References Cited

U.S. PATENT DOCUMENTS

2009/0004245 A1   1/2009  Orilla et al.
2015/0277147 A1   10/2015 Kim
2019/0380871 A1*  12/2019 Gutierrez ................. A61B 3/16

FOREIGN PATENT DOCUMENTS

| KR | 1020080018980 A | 2/2008 |
| KR | 101371685 B1 | 3/2014 |
| KR | 101427392 B1 | 8/2014 |
| KR | 101812611 B1 | 12/2017 |
| KR | 1020180038359 A | 4/2018 |
| KR | 101877312 B1 | 7/2018 |
| WO | 2006084275 A2 | 8/2006 |
| WO | 2016118933 A1 | 7/2016 |

\* cited by examiner

SMART CONTACT LENS FOR NON-INVASIVE DRUG DELIVERY

CROSS-REFERENCE TO RELATED APPLICATION

This application claims priority to Korean Patent Application No. 10-2018-0134848, filed on Nov. 6, 2018, and all the benefits accruing therefrom under 35 U.S.C. § 119, the contents of which in its entirety are herein incorporated by reference.

BACKGROUND

1. Field

The present disclosure relates to a smart contact lens for non-invasive drug delivery, and more particularly, to a smart contact lens for non-invasive drug delivery, in which drugs are delivered to the tissues in the cornea and sclera in a non-invasive manner using iontophoresis.

DESCRIPTION OF GOVERNMENT-FUNDED RESEARCH AND DEVELOPMENT

This research is made in support of biomedical technology development (Ocular-typed diabetes monitoring platform system, No. 1711073006) in the National Research Foundation of Korea, the Ministry of Science and ICT of the Republic of Korea, under the supervision of Korean Institute of Science and Technology.

2. Description of the Related Art

According to National Interest Disease Statistics of Health Insurance Review & Assessment Service, the three most common eye disorders, cataracts, glaucoma and macular degeneration, have a gradually increasing tendency of the number of patients, and among them, glaucoma and macular degeneration are mainly treated using medication. However, conventional ocular drug delivery technologies such as eyedroppers, intravitreal injections, intravitreal implantable devices and drug-containing hydrogel contact lenses involve inefficient or invasive delivery methods as below, and to overcome the limitation and disadvantage, there is a need for safer and more efficient drug delivery technology.

In the case of a hydrogel contact lens having passive drug release structure to the corneal/scleral surface using a contact lens platform, the finite element analysis performed by using COMSOL Multiphysics®, a multiphysics analysis software, reveals that although there is a difference in the loadable drug amount according to the type of hydrogel (hydrogel, silicone hydrogel), as a result, there is no significant difference in the duration of drug release delivered to the cornea or eye surface through diffusion.

The first finite element analysis is conducted on a hydrogel lens and a silicone hydrogel lens with Cyclosporin A known as a drug for treating dry eye syndrome, and is also conducted on a silicone hydrogel lens loading a small amount of drug due to adverse reactions occurring with that the release rate of Cyclosporin A is 166 ng/hr or more. Because Cyclosporin A is hydrophobic, the general silicone hydrogel lens having a large amount of silicone molecules can load the drug in a large amount, while the hydrogel lens which is hydrophilic loads the drug in a smaller amount. For the effective treatment of dry eye syndrome through Cyclosporin A, it is necessary to administer the drug above 200 ng/hr, and considering that adverse reactions may occur when the drug release rate is 166 ng/hr or more as mentioned above, it is found that the silicone hydrogel lens releases the drug in excess for the first 13 hours, and when the amount of drug reduces, the release time reduces 30% or more.

Additionally, it is found that the hydrogel lens which is hydrophilic has the drug release time of 20% level compared to silicone hydrogel due to a small drug loading amount, and in contrast, a contrary result is obtained from analysis using Timolol Maleate, which is hydrophilic, used for the treatment of glaucoma. As a result, in the drug loading using hydrogel and silicone hydrogel, it is determined that matching with the hydrophilic/hydrophobic nature of the used drug will be an important requirement.

In conclusion, contact lenses loading drugs in hydrogel/silicone hydrogel have a limitation that are still impossible to deliver the drugs to the tissues in the cornea and sclera, and in the case of continual drug delivery using the existing contact lenses, the amount of drugs actually absorbed into the tissues is notably small compared to the drug release amount (Cyclosporin A: <50%, Timolol Maleate: <5%).

Iontophoresis is a process of delivering drugs containing charged ions from the tissue surface into the tissues in a non-invasive manner by applying direct current (DC) of about 1 mA to two electrodes. The performance of ocular drug delivery technology using iontophoresis has been already proven, and there are commercial products on the market as below.

However, the currently used drug delivery using iontophoresis is used through doctors on visits to hospitals 3-4 times a month to treat inflammation caused by rejection after corneal transplant surgery, and is not practically used for drug delivery for eye disease treatment requiring periodic drug delivery. Results of delivery of glaucoma or macular degeneration related drugs to the tissues in the cornea and sclera using iontophoresis have not yet been reported, and there have been reports of the results about the rate of drug delivery to tissues (500 ng/hr) and the duration of drug release (maximum 8 hours) of glaucoma related treatment drug, Timolol Maleate, based on contact lenses.

Moreover, when a drug loaded instrument is placed on an eye as below, the eye surface may be damaged by the instrument, and for drug delivery, a patient is not allowed to blink for a predetermined time in a lying position, so safety and convenience is low.

To solve the above-described problems, there have been studies presenting drug-containing hydrogel for electrode applications that come into contact with eyes, but it is difficult to fix a few cm sized system to the eye surface, and still, portability is low and blinking is disallowed during drug injection.

SUMMARY

The present disclosure is designed to solve the above-described problem, and therefore the present disclosure is directed to providing a smart contact lens for non-invasive drug delivery using iontophoresis to allow efficient absorption and provide users with convenience and portability.

A smart contact lens for non-invasive drug delivery according to the present disclosure includes a platform configured to be worn on an eye, a reservoir installed within the platform, and having a receiving part in which a drug is received, to provide the eye with the drug, an electrode for iontophoresis installed in the reservoir to make iontophoresis work, to provide the eye with the drug from the reservoir, and an activation chip electrically connected to the electrode for iontophoresis to activate iontophoresis.

According to an example related to the present disclosure, the smart contact lens for non-invasive drug delivery according to the present disclosure may further include a power transmitting structure electrically connected to the activation chip to supply external power to the activation chip, and a power storage electrically connected to the power transmitting structure to receive the power from the power transmitting structure and store the power.

According to another example related to the present disclosure, the reservoir may include a support surface installed within the platform, a plurality of pillars extending in a direction perpendicular to the support surface, and a supply surface formed at ends of the plurality of pillars and disposed opposite the support surface with the pillars interposed between, to provide the eye with the drug.

The receiving part may be provided between the support surface and the supply surface with the pillars interposed between.

The supply surface may have a supply hole to provide the eye with the drug.

The plurality of pillars may be disposed between the support surface and the supply surface and spaced apart from each other.

DETAILED DESCRIPTION

Hereinafter, the disclosed embodiments will be described in detail with reference to the accompanying drawings, and identical or similar elements are given identical or similar reference signs and redundant descriptions are omitted herein. As used herein, the suffix "part" in the elements is only given or used to ease the drafting of the specification, and does not have any meaning or role for identifying itself. Additionally, in describing the embodiments disclosed herein, when a certain detailed description of relevant known technology is determined to render the key subject matter of the disclosed embodiments ambiguous, the detailed description is omitted herein. Additionally, the accompanying drawings are provided for an easy understanding of the disclosed embodiments, and the technical spirit disclosed herein is not limited by the accompanying drawings, and it should be understood that the present disclosure covers all modifications, equivalents or alternatives falling in the spirit and technical scope of the present disclosure.

The terms "first", "second", and the like may be used to describe various elements, but the elements are not limited by the terms. These terms are used to distinguish one element from another.

It will be further understood that when an element is referred to as being "connected to" another element, it can be directly connected to the other element or intervening elements may be present.

As used herein, the singular forms are intended to include the plural forms as well, unless the context clearly indicates otherwise.

It will be understood that the term "comprises" or "includes" when used in this specification, specifies the presence of stated features, integers, steps, operations, elements, components or groups thereof, but does not preclude the presence or addition of one or more other features, integers, steps, operations, elements, components, or groups thereof.

Figure 1A:
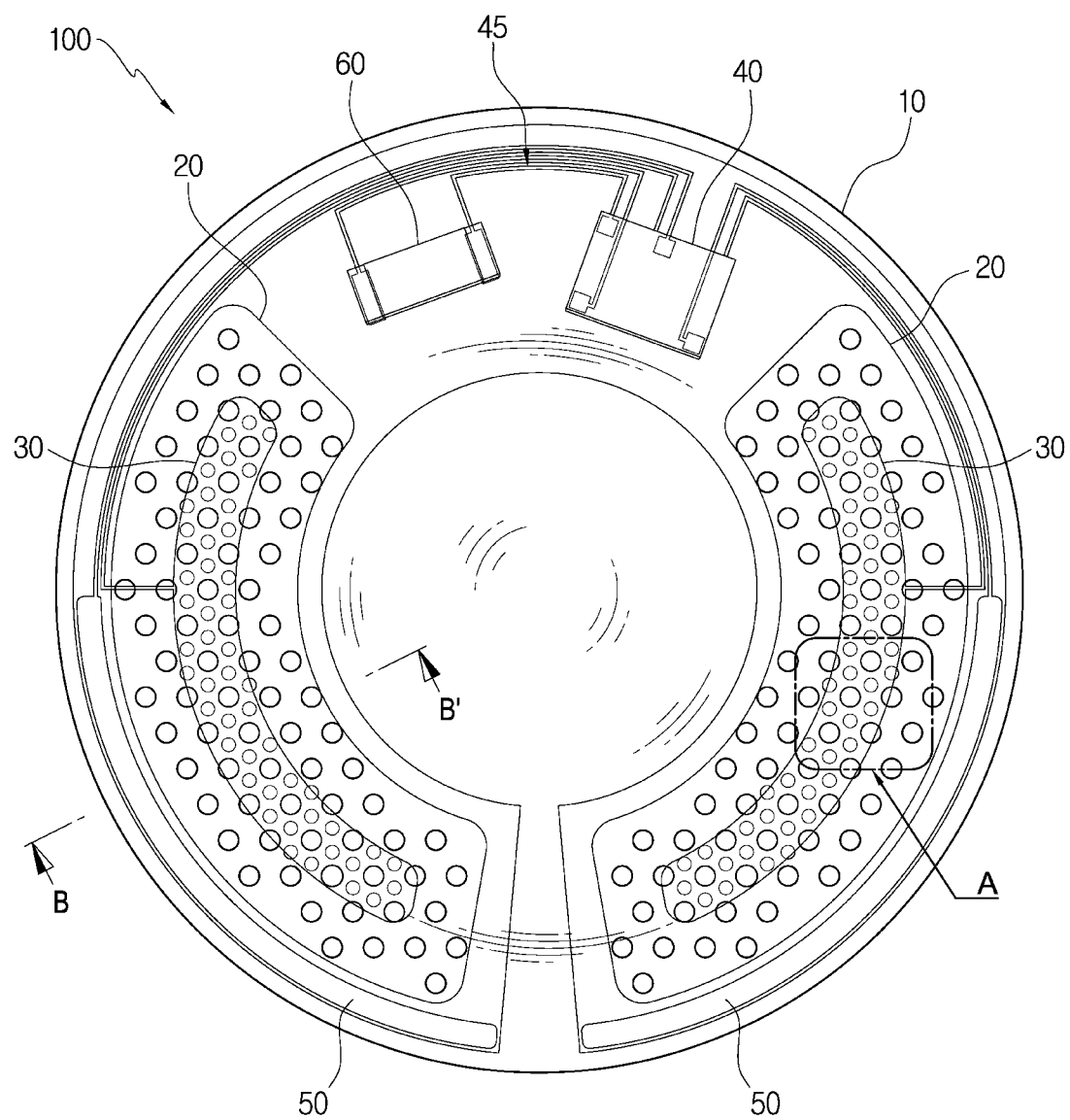
FIG. 1A is a plan view showing an example of a smart contact lens for non-invasive drug delivery according to the present disclosure.
Figure 1B:
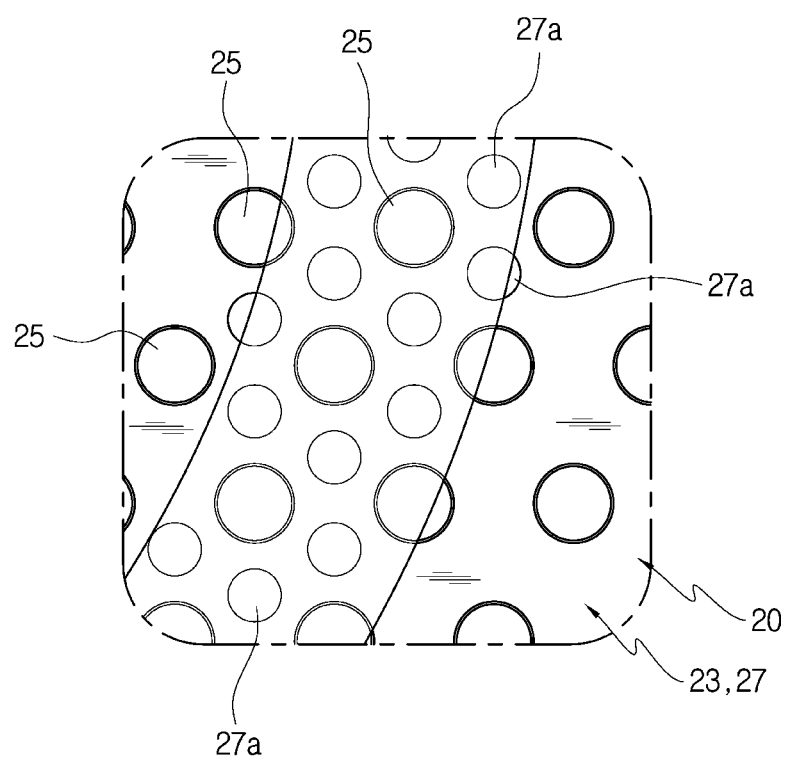
FIG. 1B is an enlarged view of section A of FIG. 1A.
Figure 1C:
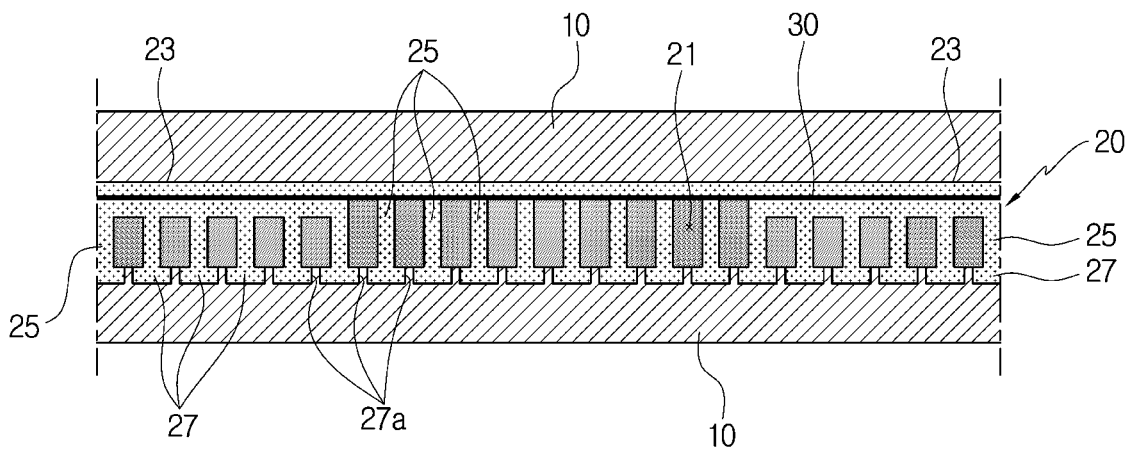
FIG. 1C is a cross-sectional view taken along the line B-B' of FIG. 1A.

FIG. 1A is a plan view showing an example of a smart contact lens 100 for non-invasive drug delivery according to the present disclosure, FIG. 1B is an enlarged view of section A of FIG. 1A, and FIG. 1C is a cross-sectional view taken along the line B-B' of FIG. 1A.

First, the smart contact lens 100 for non-invasive drug delivery according to the present disclosure is described with reference to FIGS. 1A to 1C.

The smart contact lens 100 for non-invasive drug delivery according to the present disclosure includes a platform 10, a reservoir 20, an electrode 30 for iontophoresis and an activation chip 40.

The platform 10 is configured to be worn on an eye.

For example, the platform 10 may be formed in the shape of a thin film that can be worn on the cornea or sclera according to a target location for drug administration. Additionally, the platform 10 is configured to receive the reservoir 20, the electrode 30 for iontophoresis and the activation chip 40 as described below.

Figure 2A:
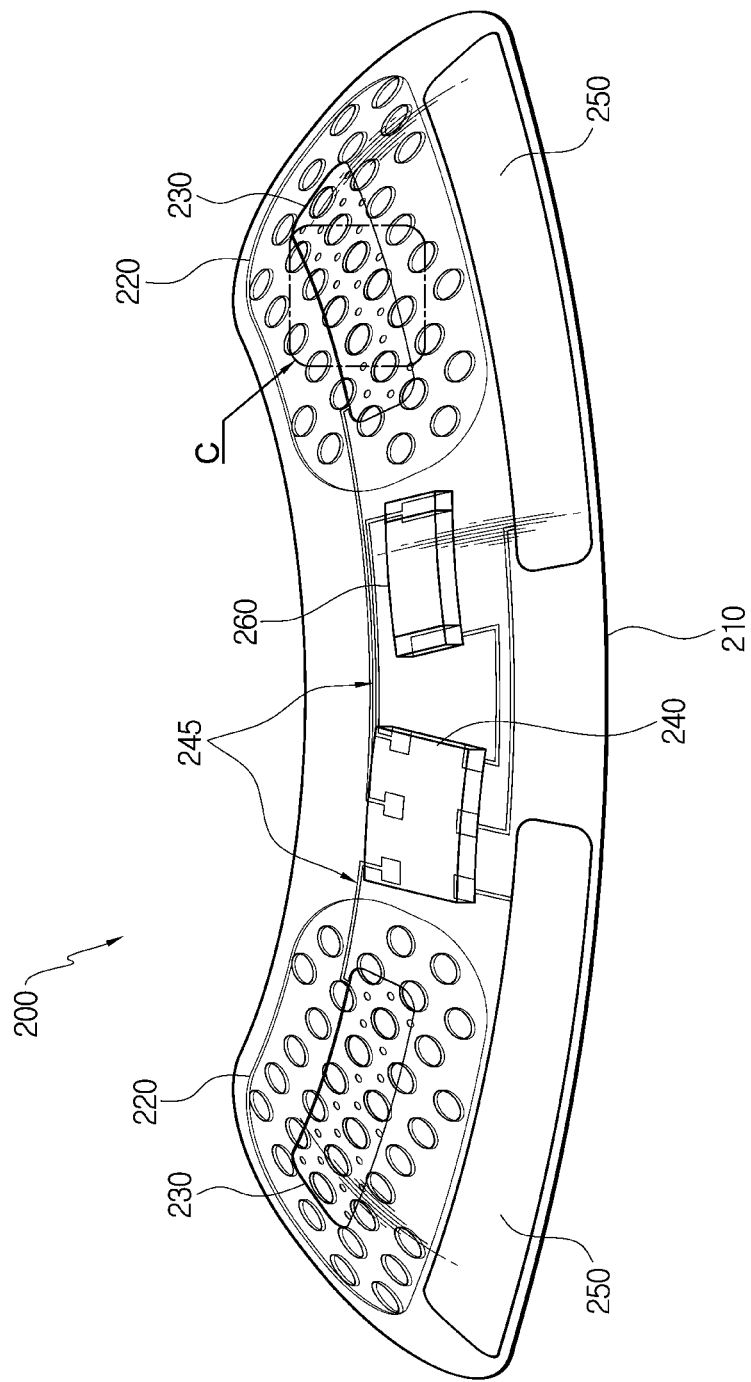
FIG. 2A is a plan view showing another example of a smart contact lens for non-invasive drug delivery according to the present disclosure.

In the case of drug administration to corneal tissues as shown in FIG. 1A, the platform 10 may be formed in a circular shape to conform to the shape of the cornea. In the case of drug administration to scleral tissues, the platform 210 may be formed in an arc shape to conform to the shape of the sclera, and this is shown in FIG. 2A, and will be described as below.

For example, the platform 10 may be made of a material such as polydimethylsiloxane (PDMS), polyvinyl alcohol (PVA) or elastomer, and may elastically deform to conform to the shape of the eye when worn.

The platform 10 may have a wire receiving part (not shown) to install a wire 45 for electrical connection of the elements described below.

The reservoir 20 is installed within the platform 10, and has a receiving part 21 in which drugs are received, to provide the eye with the drugs.

The electrode 30 for iontophoresis is installed in the reservoir 20 to make iontophoresis work, to load the drugs from the reservoir 20 to the eye.

The reservoir 20 may include a support surface 23, a plurality of pillars 25 and a supply surface 27.

The support surface 23 may be installed within the platform 10.

The plurality of pillars 25 extends in a direction perpendicular to the support surface 23 on the support surface 23, and the plurality of pillars 25 may be spaced apart from each other.

The supply surface 27 is formed at the end of the pillars 25 and disposed opposite the support surface 23 with the plurality of pillars 25 interposed between, to provide the eye with the drugs.

The supply surface 27 may have a supply hole 27a, and the drugs in the receiving part of the reservoir may be provided to the eye by the supply hole 27a.

The receiving part 21 may be provided between the support surface 23 and the supply surface 27 with the pillars 25 interposed between.

FIG. 1C shows an example of the reservoir 20 in which the support surface 23 is installed in the upper part of the platform 10, the plurality of pillars 25 extends downward on the support surface 23, and the supply surface 27 is formed at the lower end of the plurality of pillars 25.

Additionally, FIG. 1C shows an example in which the receiving parts 21 of the reservoir 20 are provided between the pillars 25, and the supply surface 27 has the supply holes 27a spaced apart from each other.

The activation chip 40 is electrically connected to the electrode 30 for iontophoresis to activate iontophoresis.

By this structure, the smart contact lens 100 for non-invasive drug delivery according to the present disclosure delivers the drugs loaded in the receiving part 21 of the reservoir 20 into the eye in iontophoresis active state.

Accordingly, the smart contact lens 100 for non-invasive drug delivery according to the present disclosure can deliver the drugs to the tissues in the cornea and sclera without damaging the eye surface.

Additionally, while the drugs are being provided, the patient does not need to lie down and is allowed to blink eyes, thereby improving safety and convenience in the provision of the drugs.

The smart contact lens 100 for non-invasive drug delivery according to the present disclosure may further include a power transmitting structure 50 and a power storage 60.

The power transmitting structure 50 is electrically connected to the activation chip 40 to supply external power to the activation chip 40. For example, the power transmitting structure 50 may wirelessly receive or supply the power. However, in the present disclosure, the power transmitting structure 50 is not necessarily limited to only wireless power transmission, and may include an electrode, an antenna or a coil.

The power storage 60 is electrically connected to the power transmitting structure 50 and is configured to receive the power from the power transmitting structure 50 and store the power.

The power storage 60 may be, for example, a capacitor, but is not necessarily limited thereto, and may be various storage devices that can receive and store power, and simply batteries may be applied.

Figure 2B:
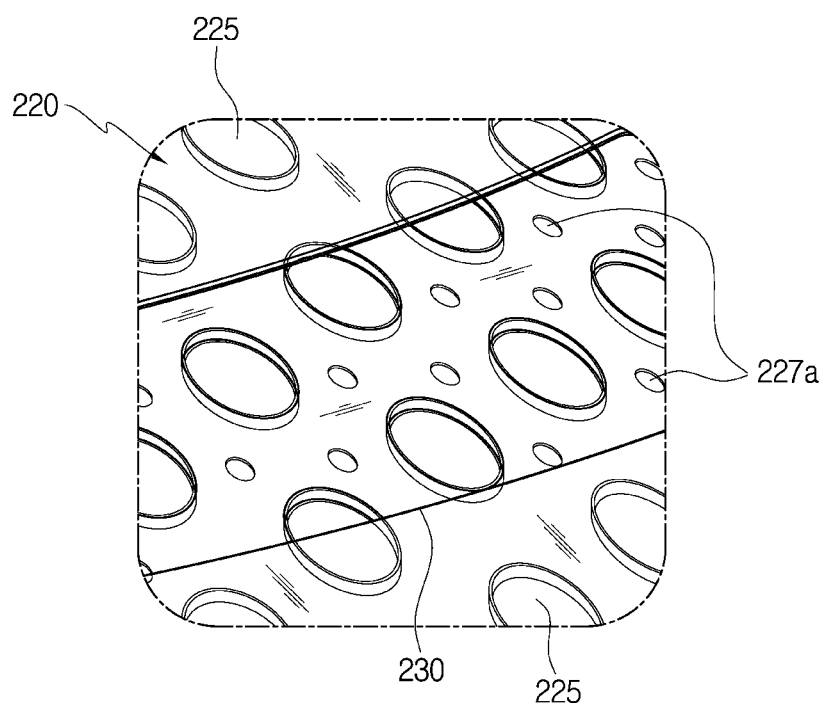
FIG. 2B is an enlarged view of section C of FIG. 2A.

FIG. 2A is a plan view showing another example of a smart contact lens 200 for non-invasive drug delivery according to the present disclosure, and FIG. 2B is an enlarged view of section C of FIG. 2A.

Hereinafter, another example of the smart contact lens 200 for non-invasive drug delivery according to the present disclosure is described with reference to FIGS. 2A and 2B. With regard to the smart contact lens 200 for non-invasive drug delivery according to the present disclosure not described hereinafter, a reference is made to the description of the smart contact lens 100 for non-invasive drug delivery as described above with reference to FIGS. 1A to 1C.

As described above, the primary difference between the smart contact lens 200 for non-invasive drug delivery as described hereinafter and the above-described smart contact lens 100 for non-invasive drug delivery is that a platform 210 is formed in the shape of a thin film that can be worn on the sclera, and the other elements are also formed in a shape that can be installed in the sclera.

The smart contact lens 200 for non-invasive drug delivery of another example of the present disclosure includes a platform 210, a reservoir 220, an electrode 230 for iontophoresis and an activation chip 240.

The platform 210 is configured to be worn on an eye.

For example, the platform 210 may be formed in the shape of a thin film that can be worn on the sclera, and referring to FIG. 2A, shown is an example of the platform 210 formed in an arc shape to conform to the shape of the sclera. Additionally, the platform 210 is configured to receive the reservoir 220, the electrode 230 for iontophoresis and the activation chip 240 as described below.

For example, the platform 210 may be made of a material such as polydimethylsiloxane (PDMS), polyvinyl alcohol (PVA) or elastomer, and may elastically deform to conform to the shape of the eye when worn.

The platform 210 may have a wire receiving part (not shown) to install a wire 245 for electrical connection of the elements described below.

The reservoir 220 is installed within the platform 210, and has a receiving part (not shown) in which drugs are received, to provide the eye with the drugs. Although the receiving part is not shown in FIGS. 2A and 2B, the receiving part or the other elements will be understood with reference to FIG. 1C.

The electrode 230 for iontophoresis is installed in the reservoir 220 to make iontophoresis work, to load the drugs from the reservoir 220 to the sclera. FIG. 2A shows an example of the reservoir 220 that is installed on each of two sides of the platform 210.

The reservoir 220 may include a support surface 223, a plurality of pillars 225 and a supply surface 227.

The support surface 223 may be installed within the platform 210.

The plurality of pillars 225 extends in a direction perpendicular to the support surface 223 on the support surface 223, and the plurality of pillars 225 may be spaced apart from each other.

The supply surface 227 is formed at the end of the pillars 225 and disposed opposite the support surface 223 with the plurality of pillars 225 interposed between, to provide the eye with the drugs.

The supply surface 227 may have a supply hole 227a, and the drugs in the receiving part of the reservoir may be provided to the eye by the supply hole 227a.

The receiving part 221 may be provided between the support surface 223 and the supply surface 227 with the pillars 225 interposed between.

The detailed structure of the reservoir 220 including the support surface 223, the plurality of pillars 225 and the supply surface 227 will be understood with reference to the smart contact lens 100 for non-invasive drug delivery of the above-described example of FIG. 1C.

The activation chip 240 is electrically connected to the electrode 230 for iontophoresis to activate iontophoresis.

By this structure, the smart contact lens 200 for non-invasive drug delivery according to the present disclosure delivers the drugs loaded in the receiving part of the reservoir 220 to the eye in iontophoresis active state.

Accordingly, the smart contact lens 200 for non-invasive drug delivery according to the present disclosure can deliver the drugs to the tissues in the cornea and sclera without damaging the eye surface.

Additionally, while the drugs are being provided, the patient does not need to lie down and is allowed to blink eyes, thereby improving safety and convenience in the provision of the drugs.

The smart contact lens 200 for non-invasive drug delivery according to the present disclosure may further include a power transmitting structure 250 and a power storage 260.

The power transmitting structure 250 is electrically connected to the activation chip 240 to supply external power to the activation chip 240. For example, the power transmitting structure 250 may wirelessly receive or supply the power.

The power storage 260 is electrically connected to the power transmitting structure 250 and is configured to receive the power from the power transmitting structure 250 and store the power.

The power storage 260 may be, for example, a capacitor, but is not necessarily limited thereto, and may be various storage devices that can receive and store power, and simply batteries may be applied.

The smart contact lens for non-invasive drug delivery according to the present disclosure delivers the drugs loaded in the reservoir to the eye in iontophoresis active state.

Additionally, the smart contact lens for non-invasive drug delivery according to the present disclosure can deliver the drugs to the tissues in the cornea and sclera without damaging the eye surface.

Additionally, the smart contact lens for non-invasive drug delivery according to the present disclosure can supply external power to the activation chip by the power transmitting structure, and store the supplied power by the power storage.

The smart contact lens 100 for non-invasive drug delivery as described hereinabove is not limited to the configuration and method of the embodiments described above, and some or all the embodiments may be selectively combined to make various modification.

It is obvious to those skilled in the art that the present disclosure may be embodied in other particular forms without departing from the spirit and essential features of the present disclosure. Therefore, the above detailed description should not be interpreted as being limiting in all aspects and should be considered as being exemplary. The scope of the present disclosure should be determined by the reasonable interpretation of the appended claims, and the scope of the present disclosure covers all modifications within the equivalent scope of the present disclosure.

[Detailed Description of Main Elements]

100, 200: Smart contact lens for non-invasive drug delivery
10, 210: Platform
20, 220: Reservoir — 21: Receiving part
23, 223: Support surface — 25, 225: Pillar
27: Supply surface
27a, 227a: Supply hole
30, 230: Electrode for iontophoresis

[Detailed Description of Main Elements]

40, 240: Activation chip
45, 245: Wire
50, 250: Power transmitting structure
60, 260: Power storage

What is claimed is:

1. A smart contact lens for non-invasive drug delivery, comprising:
   a platform configured to be worn on an eye;
   a reservoir installed within the platform, and having a receiving part in which a drug is received, to provide the eye with the drug;
   an electrode for iontophoresis installed in the reservoir to make iontophoresis work, to provide the eye with the drug from the reservoir;
   an activation chip electrically connected to the electrode for iontophoresis to activate iontophoresis,
   a power transmitting structure electrically connected to the activation chip to supply external power to the activation chip; and
   a power storage electrically connected to the power transmitting structure to receive the external power from the power transmitting structure and store the external power,
   wherein the reservoir includes:
      a support surface installed within the platform;
      a supply surface disposed opposite the support surface to provide the eye with the drug;
      a plurality of pillars interposed between the support surface and the supply surface to extend from the supply surface to the support surface in a direction perpendicular.

2. The smart contact lens for non-invasive drug delivery according to claim 1, wherein the receiving part is provided between the support surface and the supply surface with the pillars interposed between.

3. The smart contact lens for non-invasive drug delivery according to claim 1, wherein the supply surface has a supply hole to provide the eye with the drug.

4. The smart contact lens for non-invasive drug delivery according to claim 1,
   wherein the pillars are spaced apart from each other in a space between the support surface and the supply surface.

* * * * *